United States Patent [19]

Kitsukawa et al.

[11] Patent Number: 4,604,483

[45] Date of Patent: Aug. 5, 1986

[54] METHOD SEPARATING PHENYLALANINE AND CINNAMIC ACID

[75] Inventors: Tomohiko Kitsukawa; Hiroshi Kusano, both of Yokohama; Eiji Miyata, Komae; Toyokazu Sugawara, Sagamihara, all of Japan

[73] Assignee: Mitsubishi Chemical Industries Limited, Tokyo, Japan

[21] Appl. No.: 699,015

[22] Filed: Feb. 7, 1985

[30] Foreign Application Priority Data

Feb. 28, 1984 [JP] Japan ................................ 59-37050

[51] Int. Cl.$^4$ ............................................ C07C 99/12
[52] U.S. Cl. ................................................... 562/443
[58] Field of Search ................................ 562/443, 449

[56] References Cited

FOREIGN PATENT DOCUMENTS 53-96388  8/1978  Japan ................................. 562/443
45860    11/1980  Japan ................................. 562/443

OTHER PUBLICATIONS

Samejima, The Microbial Production of Amino Acids, pp. 227-259 (1972).

Primary Examiner—James H. Reamer
Attorney, Agent, or Firm—Jordan B. Bierman

[57] ABSTRACT

In a method of separating phenylalanine and cinnamic acid from a mixed solution containing phenylalanine and cinnamic acid, a method of separating phenylalanine and cinnamic acid which comprises subjecting said mixed solution to chromatographic development using a synthetic adsorbent, such as Diaion, Amberlite etc., in the presence of a salt, such as ammonium halides, ammonium sulfate, alkali metal nitrates, ammonium and alkali metal salts of fatty acids, at a concentration in the range where the salting-out effect on cinnamic acid is greater than that on phenylalanine and also both phenylalanine and cinnamic acid can be dissolved, for example, in the range of 0.2-5N.

23 Claims, 7 Drawing Figures

METHOD SEPARATING PHENYLALANINE AND CINNAMIC ACID

This application claims priority under 35 USC 119 of Japanese Patent Application No. 37050/1984, filed Feb. 28, 1984.

BACKGROUND OF THE INVENTION

1. Field of the Invention

This invention relates to a method of separating phenylalanine and cinnamic acid, and more specifically, it relates to a method of separating phenylalanine and cinnamic acid by contacting a mixed solution containing phenylalanine and cinnamic acid with a synthetic adsorbent under specific conditions.

2. Description of the Prior Art

Phenylalanine is one of essential amino acids and is used in pharmaceuticals, in particular, in medicinal amino acid transfusions etc., and recently it has aroused people's interest as an amino acid constituting $\alpha$-aspartylphenylalanine methyl ester which is a peptide type sweetener.

Phenylalanine has heretofore been produced by a chemical synthetic process, a protein hydrolytic process, a fermentation process etc., but the production efficiency was low with any such process and efficient production processes have been studied.

As one of these processes, there is a process for producing L-phenylalanine from cinnamic acid as a starting material by an enzymatic reaction using L-phenylalanine ammonialyase in the presence of ammonia, and this process has been attracting attention as an industrial production process because the productivity of phenylalanine is extremely high.

However, in the above-described process, the produced L-phenylalanine is co-present with cinnamic acid and ammonia, and therefore, in order to obtain the L-phenylalanine as a single substance, it is necessary to separate and recover the L-phenylalanine from the mixture of those. But, since the phenylalanine and the cinnamic acid are similar in structure, it is difficult to separate them from each other. Therefore, in order to industrially advantageously produce L-phenylalanine, it is important to efficiently conduct the separation from the co-present cinnamic acid.

Under such circumstances, the present inventors have been intensively studying in pursuit of a method of efficiently separating and purifying phenylalanine co-present with cinnamic acid, and have discovered that by conducting treatment using a porous synthetic adsorbent under specific conditions, the separation of phenylalanine and cinnamic acid can be extremely efficiently achieved.

The porous synthetic adsorbent is composed of a crosslinked polymer obtained by polymerizing, polycondensing or co-polymerizing various organic polymeric monomers, or a crosslinked polymer obtained by polymerizing or polycondensing various polymeric monomers and thereafter crosslinking, and has significant levels of surface area and pore volume, and is utilized in the separation and purification of various substances, in particular, medicines, foods etc. Examples of the synthetic adsorbent are abundant, and, for example, they have been produced and found in market under such tradenames as "Diaion" HP 10, 20, 21, 30, 40, 50, "Diaion" HP 2 MG (produced by Mitsubishi Chemical Industries, Ltd.; trademark), "Amberlite" XAD 2, 4, 7, 8 (produced by Rohm & Haas Co., U.S.A.; trademark) etc.

It is already known that such synthetic adsorbents satisfactorily adsorb amino acids and organic acids; for example, it is also known that the amino acids are most favorably adsorbed in the vicinity of the isoelectric point, while the organic acids are well adsorbed under low pH conditions, i.e., where the organic acid is not dissociated.

Based on such a knowledge, the present inventors have been intensively studying on a method of separating and purifying phenylalanine from a mixed solution containing phenylalanine and cinnamic acid using a synthetic adsorbent, and, as a result, have come to discover that the adsorptions of phenylalanine and cinnamic acid by a synthetic adsorbent depend on the concentration of a co-present salt, and, surprisingly, the relative adsorption (selectivity in adsorption) of phenylalanine relative to cinnamic acid greatly varies depending on the concentration of the co-present salt, and therefore that by wisely utilizing these phenomenons, the separation of phenylalanine and cinnamic acid may be extremely efficiently effected, thereby having accomplished this invention.

SUMMARY OF THE INVENTION

Accordingly, this invention presents an industrially advantageous method of separating and purifying phenylalanine co-present with cinnamic acid, and its gist resides in a method of separating phenylalanine and cinnamic acid from a mixed solution containing phenylalanine and cinnamic acid, which method comprises subjecting said mixed solution to chromatographic development using a synthetic adsorbent in the presence of a salt at a concentration in the range where the salting-out effect on cinnamic acid is greater than that on phenylalanine and also both phenylalanine and cinnamic acid can be dissolved.

BRIEF DESCRIPTION OF THE DRAWING

FIG. 2-A is a graph showing the relative adsorption of phenylalanine relative to cinnamic acid in Reference Example 1 as a function of the salt in the solution. In the figure, the ordinate indicates the relative adsorption and the abscissa indicates the concentration of the salt. In the figure, (a) shows the results when the pH of the solution was 10 and (b) shows those when the pH of the solution was 7.

FIG. 2-B is a graph showing the relative adsorption of Phenylalanine relative to cinnamic acid in Reference Example 2 as a function of the salt concentration in the solution, in which the ordinate indicates the relative adsorption and the abscissa indicates the salt concentration. In the figure, (a) shows the results when ammonium sulfate was used as the salt, (b) for sodium nitrate, (c) for diammonium citrate, (d) for sodium citrate and (e) for sodium acetate.

DETAILED DESCRIPTION OF THE PREFERRED EMBODIMENTS

This invention is to separate phenylalanine and cinnamic acid using a synthetic adsorbent, and when a mixed solution containing both phenylalanine and cinnamic acid is contacted with a synthetic adsorbent, the amounts of both adsorbed to the adsorbent and the relative adsorption thereof greatly vary depending on the concentrations of phenylalanine and cinnamic acid, the concentration of a co-present salt, the conditions of the solution, e.g., the pH etc. of the solution and so forth, especially, the concentration of the co-present salt.

Figure 1:
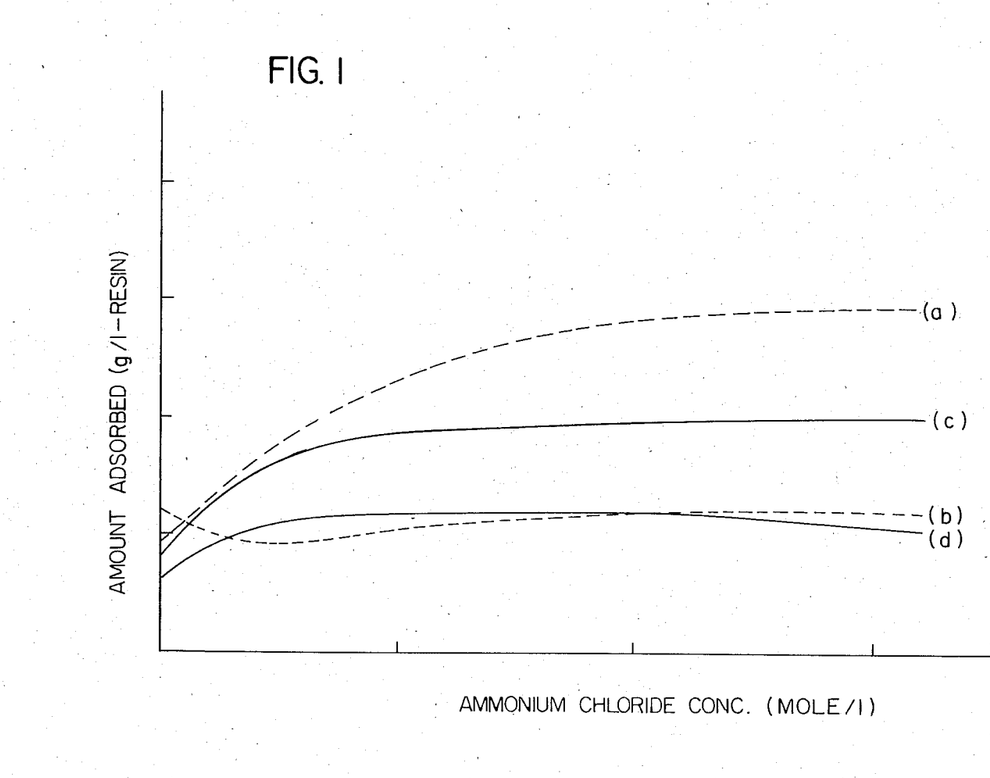
FIG. 1 is a graph showing the relationships between the amounts of phenylalanine and cinnamic acid adsorbed and the concentration of ammonium chloride in the solution when ammonium chloride solutions having various concentrations and containing phenylalanine and cinnamic acid were contacted with a synthetic adsorbent Diaion HP 20 according to Reference Example 1, in which the abscissa indicates the concentration of the salt in the solution and the ordinate indicates the amount adsorbed. In the figure, (a) and (b) represent cinnamic acid and phenylalanine respectively when the pH of the solution was 7, and (c) and (d) represent cinnamic acid and phenylalanine respectively when the pH of the solution was 10.
Figure 2:
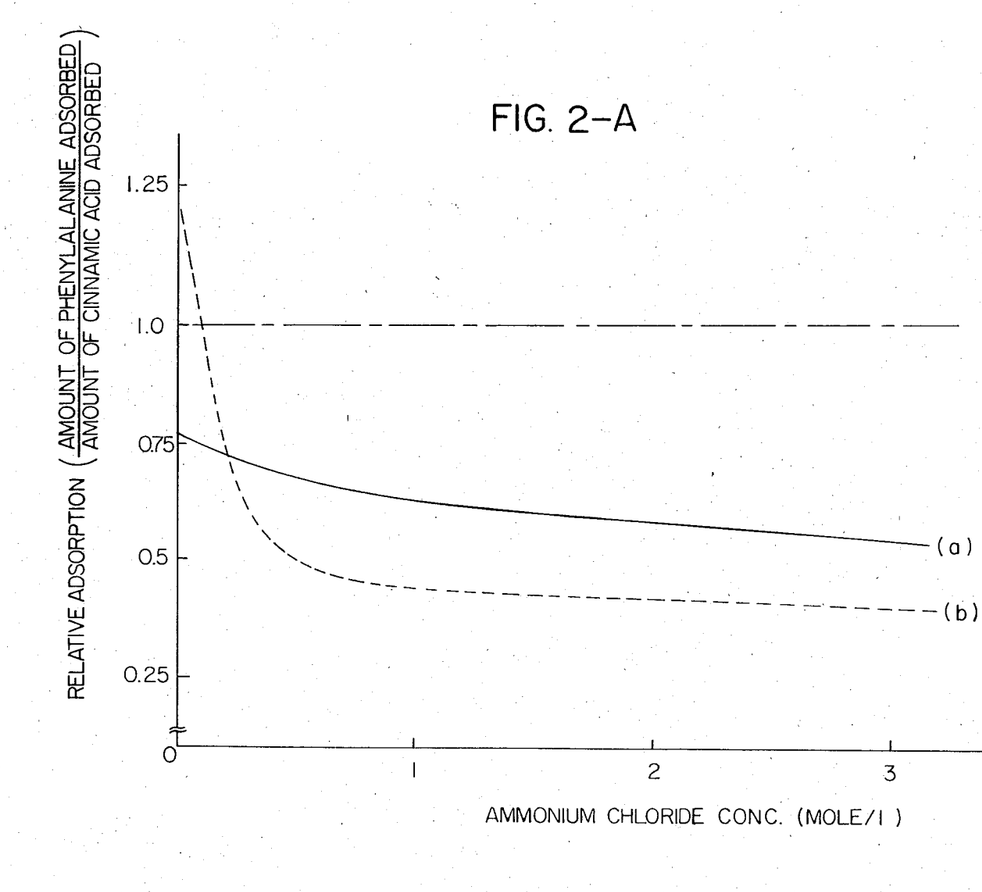

For example, FIG. 1 shows the amounts of phenylalanine and cinnamic acid adsorbed when 50 ml of a synthetic adsorbent Diaion HP 20 was added to one liter of a solution containing 5 g of each of Reagent Special Grade phenylalanine and cinnamic acid and a predetermined amount of ammonium chloride as a salt and adjusted to a predetermined pH with ammonia. Further, FIG. 2-A shows the relative adsorption of phenylalanine relative to cinnamic acid under the same conditions as in FIG. 1, expressed as the ratio of the amount of phenylalanine adsorbed relative to the amount of cinnamic acid adsorbed taken as 1.

As is clear from FIG. 1, although the amount of phenylalanine adsorbed to the synthetic adsorbent depends on the concentration of the ammonium chloride in the solution, the degree of change in the amount adsorbed is small, whereas the amount of cinnamic acid adsorbed also depends on the salt concentration in the solution and moreover the degree of change is much greater than the case of phenylalanine and, in particular, at a salt concentration of 0.2N or higher, preferably 0.5N or higher, cinnamic acid is adsorbed better than phenylalanine. Therefore, by adjusting the concentration of the co-present salt, it is possible to separate phenylalanine and cinnamic acid from each other by changing the relative adsorption of phenylalanine relative to cinnamic acid as shown in FIG. 2.

The above-described phenomenon that the relative adsorption of phenylalanine relative to cinnamic acid varies depending on the salt concentration means that the salting-out effect on cinnamic acid by the salt (the effect to reduce the solubility by the time to salting-out) is greater than that on phenylalanine, and this invention utilizes the difference in such salting-out effect, thereby phenylalanine may be separated and purified from a mixed solution containing phenylalanine and cinnamic acid.

The above-described salting-out effect may be achieved by the use of various salts including ammonium chloride, as well as organic salts.

FIG. 2-B is a graph showing the relative adsorption of phenylalanine relative to cinnamic acid when various salts were used, (b) sodium nitrate, (c) diammonium citrate, (d) sodium citrate and (e) sodium acetate.

The solution containing phenylalanine and cinnamic acid to be treated to separate according to the method of this invention is not particularly restricted, and the concentrations of phenylalanine and cinnamic acid in the solution are generally about 0.05-20 weight/volume percent respectively. The concentration of the salt in the solution is appropriately selected from the range in which both phenylalanine and cinnamic acid are dissolved, taking into consideration the relative adsorption of phenylalanine relative to cinnamic acid by the salt to be used. In general, the concentration is 0.2N or higher, preferably 0.5N or higher. However, where there is meployed a method of separating phenylalanine and cinnamic acid by supplying a certain amount of a mixed solution containing phenylalanine and cinnamic acid to a column packed with a synthetic adsorbent and conducting elution development chromatography by passing a different solution containing substantially no phenylalanine or cinnamic acid as an eluant, it is not necessary that the salt concentration in the mixed solution of phenylalanine and cinnamic acid be 0.2N or higher, and it is sufficient that the salt concentration in the eluant, which serves as a solvent for the most time during the contact of the phenylalanine and the cinnamic acid with the synthetic adsorbent, be 0.2N or higher. If the salt concentration is less than 0.2N, the difference in adsorption between phenylalanine and cinnamic acid to the adsorbent is not great enough and thus the separation is difficult. As the salt, there may be employed, for example, combinations of a proton selected from ammonium ion and alkali metal ions and an anion selected from halogen ions, sulfate ion, nitrate ion, phosphate ion, carbonate ion and aliphatic carboxylate ions, and in particular, ammonium halides, ammonium sulfate, alkali metal nitrates, ammonium salts and alkali metal salts of fatty acids, etc. are preferred. The pH of these solutions is not particularly restricted, but since there is a tendency that the higher the pH, the lower the adsorption, in particular, the adsorption of cinnamic acid, it is advised to maintain the pH of the solution at 4–12, preferably 5–11.

The synthetic adsorbent used in this invention is a cross-linked polymer obtained by polymerizing, copolymerizing or polycondensing various organic polymeric monomers or a crosslinked polymer obtained by polymerizing or polycondensing various polymeric monomers and thereafter crosslinking, such crosslinked polymer having significant levels of surface area and pore volume. The adsorption of the synthetic adsorbent is greatly influenced by its surface area and pore volume, and it is desired to use that having a surface area of at least 100 m$^2$/g, preferably 300 m$^2$/g or more, and a pore volume of at least 0.1 ml/g, preferably 0.5 ml/g or more. On the other hand, as the unit structure constituting the basic body of the synthetic adsorbent is preferably that having a basic structure composed of an aromatic copolymer based on styrene and divinylbenzene from a viewpoint of the adsorption capacity. Commercial examples of such a synthetic adsorbent are "Diaion" HP 10, 20, 21, 30, 40, 50 (produced by Mitsubishi Chemical Industries, Ltd.; registered trademark), "Amberlite" XAD 2, 4 (produced by Rohm & Haas Co., U.S.A.; trademark) etc.

The specific operational method for separating phenylalanine and cinnamic acid on carrying out the method of this invention is not particularly restricted as long as the contact with the synthetic adsorbent is effected under conditions that the concentration of the salt in the mixed solution is substantially 0.2N or higher, but in order to effectively conduct the separation, it is preferred to carry out chromatographic separation by packing a synthetic adsorbent into a column and passing a solution containing phenylalanine and cinnamic acid through this packed column.

On that occasion, when the mixed solution containing phenylalanine and cinnamic acid and having a salt concentration of 0.2N or higher is continuously supplied to the packed layer of the synthetic adsorbent, since phenylalanine having weak adsorption is eluted first and cinnamic acid later starts to elute, it is possible to obtain phenylalanine free from cinnamic acid by recovering the fractions from the point when the phenylalanine has started to elute until just before the cinnamic acid starts to elute, that is, by the so-called front chromatographic separation. At that time, the salt co-present in the original solution enhances the adsorptions of phenylalanine and cinnamic acid to the synthetic adsorbent but it is itself hardly adsorbed to the synthetic adsorbent and starts to elute prior to the elution of the phenylalanine, and therefore it is also possible to recover the salt by collecting these eluted fractions. Further, when supplying of this original solution to the packed layer is continued, the adsorption by the synthetic adsorbent reaches saturation and the compositions of the solutions coming into and out of the column become equal, and in general, passing of the solution is terminated at an appropriate point either before or after the cinnamic acid starts to elute, and the most part of the cinnamic acid adsorbed to the synthetic adsorbent at that point and the remaining phenylalanine other than that already eluted are then eluted by passing, for example, a 0.1–5N, preferably 0.5–2N, ammonia or sodium hydroxide aqueous solution, thereby cinnamic acid having a reduced content of phenylalanine may be obtained. On the other hand, the synthetic adsorbent after treating with the eluant may of course be reused for the separation of phenylalanine and cinnamic acid.

As another method for the chromatographic separation using a packed layer of a synthetic adsorbent, it is also possible to conduct chromatographic development and elution by supplying a certain amount of a solution containing phenylalanine and cinnamic acid to a packed layer, and passing a solution having a salt concentration of 0.2N or higher as an eluant. On that occasion, it is not always necessary that the salt concentration of the mixed solution containing phenylalanine and cinnamic acid be 0.2N or higher, but it is sufficient that the salt concentration of the eluant comprising the most part of the solution contacted with the synthetic adsorbent in the separating step and substantially dominating the separation be 0.2N or higher.

In these methods, although the height of the packed layer of the synthetic adsorbent is preferably as high as possible considering the apparatus and operations, a height of about 0.5–5 m is generally employed. The flow rate for passing the solution is preferably about 0.1–10 m/hr in LV (space linear velocity). Where the separation is effected by chromatographic development and elution, the load of the mixed solution on the packed layer is, although somewhat depending on the concentrations of the respective components in the mixed solution and the required degree of separation, generally in the range of about 0.05–100 times the amount of the packed synthetic adsorbent from when the mixed solution has been supplied to the packed layer until cinnamic acid starts to elute from the column.

According to the method of this invention, since cinnamic acid is more strongly adsorbed to the synthetic adsorbent than phenylalanine, for example, if a mode of front chromatographic separation is employed, it is possible to obtain phenylalanine from which cinnamic acid has been completely removed may be obtained by adsorbing and removing cinnamic acid from the solution containing phenylalanine and cinnamic acid. The concentration of the phenylalanine in the solution obtained on that occasion has been hardly diluted as compared with the original solution, but on the contrary, since the phenylalanine once adsorbed to the synthetic adsorbent is substituted by cinnamic acid having stronger adsorption and liberated, there is an advantage that this may be recovered with a higher concentration than that of the original solution.

On the other hand, by employing a mode of elution chromatography according to the method of this invention, as compared with the case where the solution is eluted with desalted water containing no salt, the elution of cinnamic acid is greatly retarded and thus phenylalanine and cinnamic acid may be separated at high yields and high purities.

This invention is more particularly described by the following examples and reference examples, but it will be understood that the variations and modifications can be effected within the spirit and scope of the invention.

REFERENCE EXAMPLE 1

5 g of each of L-phenylalanine and trans-cinnamic acid, both designated as Reagent Special Grade, was dissolved in ammonium chloride aqueous solutions of various concentrations, the pH of each solution was then adjusted to 7 or 10 with ammonia water, and the total volume of each solution was made one liter. To each solution was added a synthetic adsorbent Diaion HP20, which had been prepared by taking 50 ml thereof in water and removing the water content by a centrifugal separator, and shaken in a constant temperature shaker at 30° C. for 10 hours. The concentrations of the phenylalanine and cinnamic acid remaining in the solution were measured and the amounts adsorbed to Diaion HP20 were determined from the difference from the original solution.

These results are given in FIG. 1 and FIG. 2-A as the relationships between the concentration of the salt in the solution and the amounts of phenylalanine and cinnamic acid adsorbed, and between that and the relative adsorption of phenylalanine relative to cinnamic acid (that is, the ratio of the amount of phenylalanine adsorbed to Diaion HP20 to the amount of cinnamic acid adsorbed thereto).

REFERENCE EXAMPLE 2

The amounts of phenylalanine and cinnamic acid adsorbed to Diaion HP 20 at pH 7 were determined according to the method in Reference Example 1 except that the ammonium chloride aqueous solution in Reference 1 was replaced by solutions of (a) ammonium sulfate, (b) sodium nitrate, (c) diammonium citrate, (d) sodium citrate and (e) sodium acetate.

These results are given in FIG. 2-B as the relationship between the salt concentration and the relative adsorption of phenylalanine relative to cinnamic acid.

REFERENCE EXAMPLE 3

1.0 liter of a synthetic adsorbent Diaion HP20 was packed into an acrylic resin column of 30 mm in inner diameter and 1.5 m in height.

Figure 3:
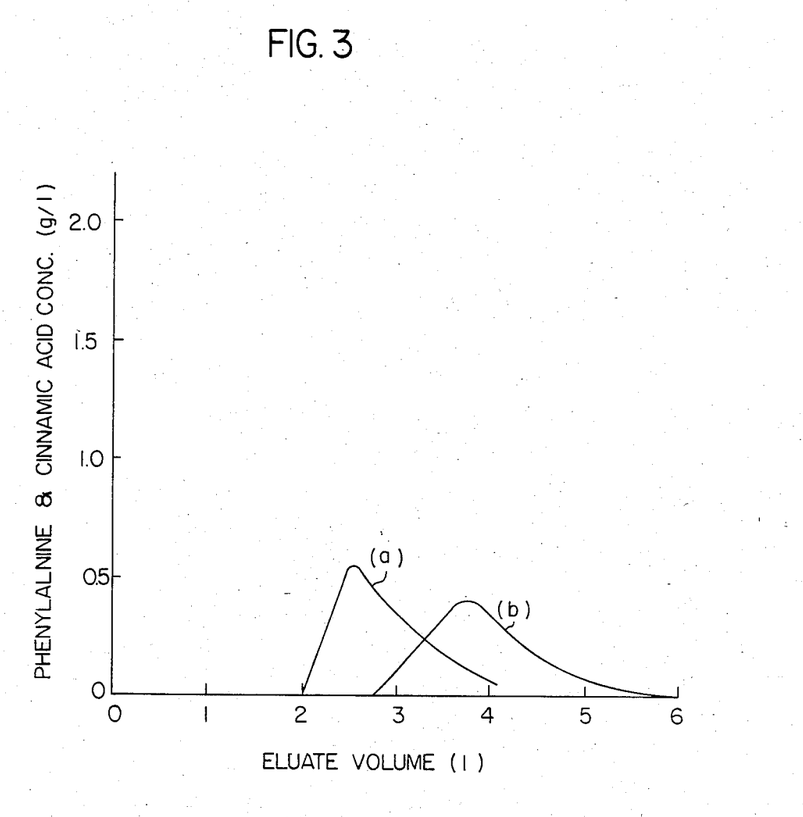
FIG. 3 is a graph showing the concentrations of the respective components in the eluate as the ordinate and the eluate volume as the abscissa when a mixed solution containing phenylalanine and cinnamic acid was eluted and developed on a column of a synthetic adsorbent Diaion HP 20 using desalted water according to Reference Example 3. In the figure, (a) is for cinnamic acid and (b) for phenylalanine.

L-Phenylalanine and trans-cinnamic acid were dissolved in ammonia water to prepare a mixture solution containing 5 g/l of L-phenylalanine, 5 g/l of trans-cinnamic acid and ammonia and having a pH of 10.0, 100 ml of which was passed through the above-described column from the top at a flow rate of 2 l/hr, and thereafter desalted water (pH 6.5) as an eluant was passed at a flow rate of 2 l/hr. The relationships between the column eluate volume (abscissa) and the concentrations of the respective components (ordinate) are given in FIG. 3. In the figure, (a) represents cinnamic acid and (b) phenylalanine.

EXAMPLE 1

Figure 4:
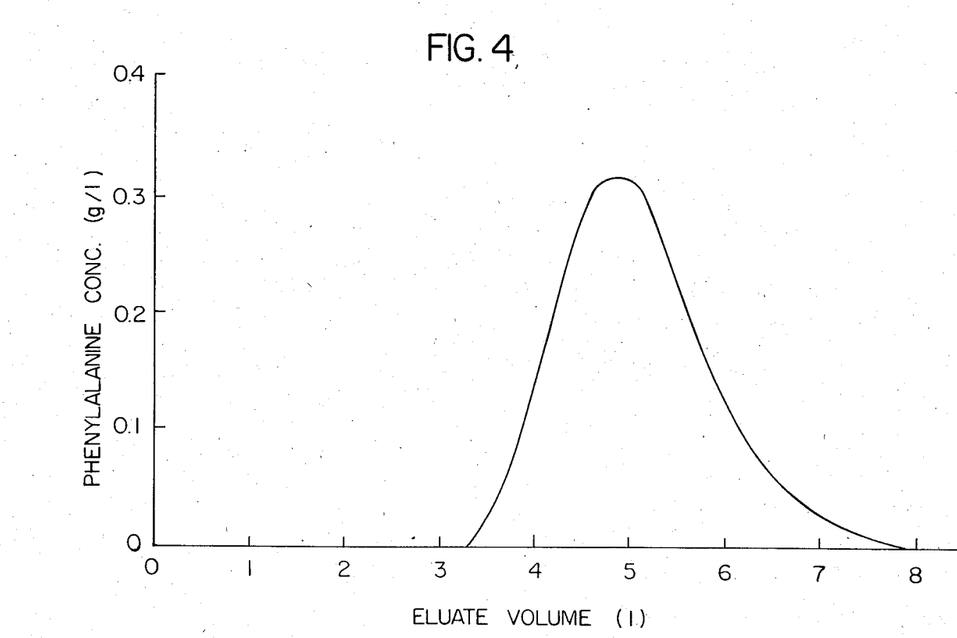
FIG. 4 is a graph showing the concentrations of the respective components in the eluate as the ordinate and the eluate volume as the abscissa when a mixed solution containing phenylalanine and cinnamic acid was eluted and developed with a 0.4N ammonium chloride aqueous solution of a pH of 7.5 through a column of a synthetic adsorbent Diaion HP 20 according to Example 1.

FIG. 4 shows the results obtained when passing 8 l of an eluant on conducting procedures similar to those in Reference Example 3 except that the desalted water as the eluant in Reference Example 3 was replaced by a 0.4N ammonium chloride aqueous solution adjusted to pH 7.5 with ammonia.

When compared with Reference Example 3, the order of the elution of phenylalanine and cinnamic acid was reversed, the elution points for both components were retarded, and especially, cinnamic acid did not elute at all even when the elution of phenylalanine had been completed, i.e. when 8 l of the eluant had been passed, thereby it was possible to recover phenylalanine completely free from cinnamic acid.

REFERENCE EXAMPLE 4

After passing 8 l of an eluate through a column as in Example 1, 1N ammonia water was passed through the column from the top at a flow rate of 2 l/hr. The relationship of the column eluate volume (abscissa) and the eluate concentration (ordinate) on that occasion is given in FIG. 5.

As a result, the cinnamic acid not eluted in Example 1 was eluted and recovered as cinnamic acid free from phenylalanine.

EXAMPLE 2

250 ml of a synthetic adsorbent Diaion HP21 was packed into an acrylic resin column of 15 mm in inner diameter and 1.5 m in height.

Figure 5:
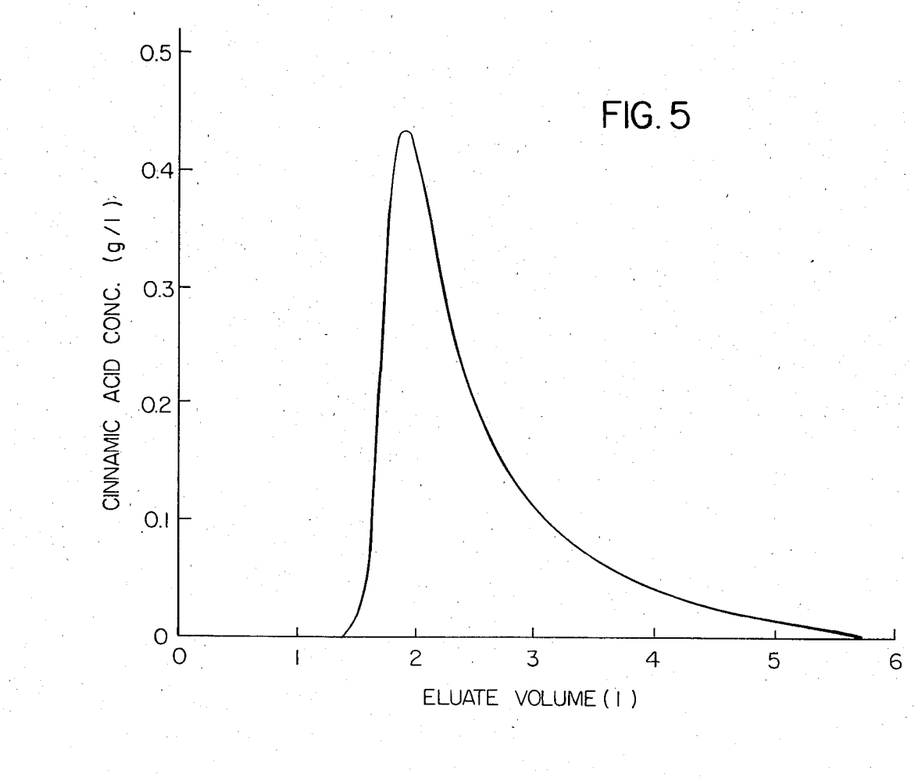
FIG. 5 is a graph showing the concentrations of the respective components in the eluate as the ordinate and the eluate volume as the abscissa when 1N ammonia water was passed according to Reference Example 4.
Figure 6:
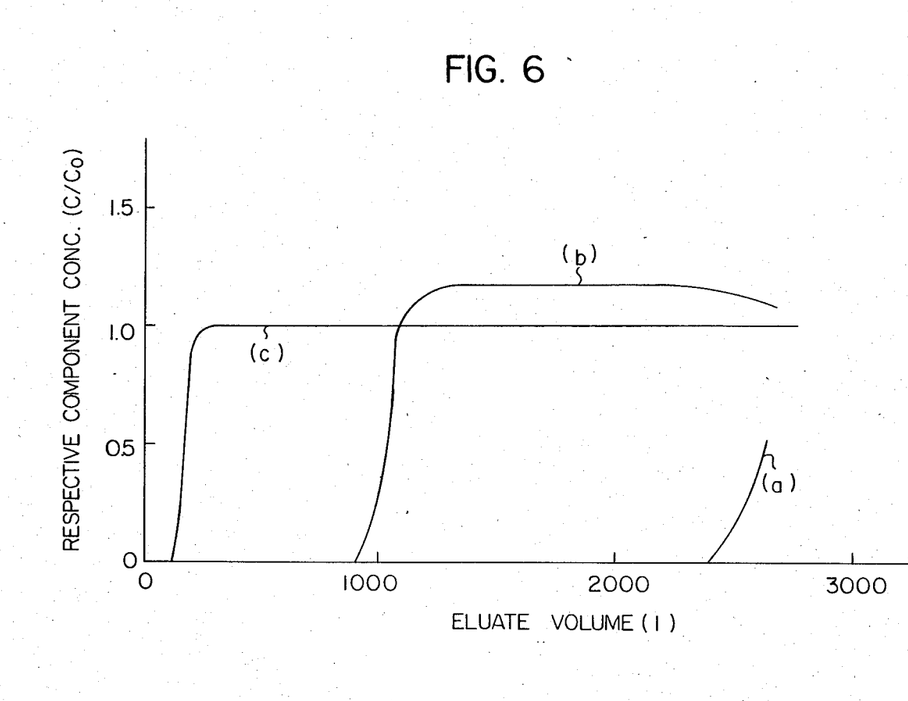
FIG. 6 is a graph showing the concentrations of the respective components in the column eluate (C) expressed as the ratios to the concentrations in the original solution ($C_o$) when a mixed solution containing phenylalanine and cinnamic acid was separated by front chromatography using a column of a synthetic adsorbent Diaion HP 21 according to Example 1. In the figure, (a) represents the concentration of cinnamic acid, (b) phenylalanine and (c) ammonium chloride and ammonia.

A solution containing 5.6 g/l of L-phenylalanine, 5 g/l of trans-cinnamic acid and 100 g/l (1.9N) of ammonium chloride and adjusted to pH 7.5 with ammonia was prepared and injected into the aforesaid column from the top at a flow rate of 500 ml/hr. The results of the measurement of the concentrations of the respective components in the eluate from the column bottom are shown in FIG. 5. An ammonium chloride solution not containing cinnamic acid or phenylalanine was recovered between 125 ml and 900 ml of the eluate, and subsequently 9.2 g of phenylalanine not containing cinnamic acid was recovered between 900 ml and 2380 ml.

What is claimed is:

1. A method of separating phenylalanine from an aqueous solution containing said phenylalamine and cinnamic acid as main components, which method comprises passing said solution through a packed layer of at least one synthetic adsorbant which is a cross-linked copolymer having a surface area of at least 100 m²/g and a pore volume of at least 0.1 ml/g in the presence of a salt, a cation selected from an ammonium ion or an alkali metal ion and an anion selected from halogen, carbonate, or an aliphatic carboxylate at a concentration of 0.1N to 5N, and recovering a fraction of said phenylalanine substantially free from said cinnamic acid.

2. The method of claim 1 wherein said salt is in said solution.

3. The method of claim 1 further comprising supplying said solution to the packed layer and eluting with an aqueous solution containing said salt at said concentration.

4. The method of claim 1 wherein said salt is one or more salts selected from ammonium halides, ammonium sulfate, alkali metal nitrates, ammonium and alkali metal salts of fatty acids.

5. The method of claim 2 wherein said salt is one or more salts selected from ammonium halides, ammonium sulfate, alkali metal nitrates, ammonium and alkali metal salts of fatty acids.

6. The method fo claim 3 wherein said salt is one or more salts selected from ammonium halides, ammonium sulfate, alkali metal nitrates, ammonium and alkali metal salts of fatty acids.

7. The method of claim 1 wherein the synthetic adsorbant has a surface area of 100 to 1.500 m²/g and a pore volume of 0.1 to 1.5 ml/g.

8. The method of claim 2 wherein the synthetic adsorbant has a surface area of 100 to 1,500 m²/g and a pore volume of 0.1 to 1.5 ml/g.

9. The method of claim 3 wherein the synthetic adsorbant has a surface area of 100 to 1,500 m²/g and a pore volume of 0.1 to 1.5 ml/g.

10. The method of claim 1 wherein the mixed aqueous solution is at a temperature of 10° to 50° C.

11. The method of claim 2 wherein the mixed aqueous solution is at a temperature of 10° to 50° C.

12. The method of claim 3 wherein the mixed aqueous solution is at a temperature of 10° to 50° C.

13. The method of claim 3, wherein said solution is supplied to the packed layer and eluted with an aqueous solution containing said salt at said concentration, whereby a salt fraction, a phenylalanine fraction, and a cinnamic acid fraction are recovered serially.

14. The method of claim 2, wherein said solution is supplied to the packed layer and eluted with an aqueous solution containing said salt at said concentration, whereby a salt fraction, a phenylalanine fraction, and a cinnamic acid fraction are recovered serially.

15. The method of claim 1 wherein the flow rate for passing the solution is about 0.1 to 10 m/hr in LV.

16. The method of claim 2 wherein the flow rate for passing the solution is about 0.1 to 10 m/hr in LV.

17. The method of claim 3 wherein the flow rate for passing the solution is about 0.1 to 10 m/hr in LV.

18. The method of claim 1 wherein the concentration of the salt is 0.5 to 2N.

19. The method of claim 2 wherein the concentration of the salt is 0.5 to 2N.

20. The method of claim 3 wherein the concentration of the salt is 0.5 to 2N.

21. The method of claim 1 wherein the concentrations of phenylalanine and cinnamic acid in the mixed solution are each 0.05 to 20 weight/volume percent.

22. The method of claim 2 wherein the concentrations of phenylalanine and cinnamic acid in the mixed solution are each 0.05 to 20 weight/volume percent.

23. The method of claim 3 wherein the concentrations of phenylalanine and cinnamic acid in the mixed solution are each 0.05 to 20 weight/volume percent.

* * * * *